(12) United States Patent
Issac et al.

(10) Patent No.: US 11,524,175 B2
(45) Date of Patent: Dec. 13, 2022

(54) INFANT WARMER USING LASER SOURCE

(71) Applicant: GE Precision Healthcare LLC, Wauwatosa, WI (US)

(72) Inventors: Robin M. Issac, Bangalore (IN); Steven M. Falk, Baltimore, MD (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/130,845

(22) Filed: Dec. 22, 2020

(65) Prior Publication Data

US 2022/0193446 A1   Jun. 23, 2022

(51) Int. Cl.
*A61N 5/06* (2006.01)
*A61N 5/067* (2006.01)

(52) U.S. Cl.
CPC ............ *A61N 5/0625* (2013.01); *A61N 5/067* (2021.08); *A61N 2005/063* (2013.01); *A61N 2005/0626* (2013.01); *A61N 2005/0643* (2013.01); *A61N 2005/0651* (2013.01); *A61N 2005/0664* (2013.01)

(58) Field of Classification Search
CPC .................. A61N 5/0625; A61N 5/067; A61N 2005/0626; A61N 2005/063; A61N 2005/0643; A61N 2005/0651; A61N 2005/0664
See application file for complete search history.

(56) References Cited

U.S. PATENT DOCUMENTS

| | | | | |
|---|---|---|---|---|
| 5,005,108 A | * | 4/1991 | Pristash | G02B 6/0061 362/23.15 |
| 2007/0208395 A1 | * | 9/2007 | Leclerc | A61N 5/0616 607/86 |
| 2018/0256426 A1 | * | 9/2018 | N | A61G 11/004 |

FOREIGN PATENT DOCUMENTS

FR   2958171 A1 * 10/2011 ........... A61N 5/0621

* cited by examiner

*Primary Examiner* — Carl H Layno
*Assistant Examiner* — Aya Ziad Bakkar
(74) *Attorney, Agent, or Firm* — Andrus Intellectual Property Law, LLP

(57) ABSTRACT

An infant treatment device includes a light source and a blanket. When the treatment device is configured to warm an infant, a laser diode is used to provide warming light. The warming light passes along an optic cable having a plurality of optic fibers each having a fiber ending. The fiber endings are spaced along is diffuser. The diffuser is designed to spread the warming light to create multiple heating zones. A control circuit is used to control the operation of the laser diode. The treatment device is designed such that the light source and blanket can be separated and connected when desired such that the light source can be used with more than one blanket. In another embodiment, the light source can include a diode design for use in phototherapy treatment.

13 Claims, 4 Drawing Sheets

INFANT WARMER USING LASER SOURCE

BACKGROUND

The presently disclosed system generally relates to a radiant heater for use with an infant patient. More specifically, the present disclosure relates to a radiant heater that includes a blanket and laser light source connected to an optical fiber cable to create the source of heat for the infant.

Traditional infant warmers work on the principle of radiant heat transfer from a NiChrome element encapsulated in ceramic or other metallic elements using a reflector to minimize the energy loss and improve the uniformity on the patient mattress to an infant. However, these prior art infant warmers are very inefficient because a 300-540 W source is needed to provide a wattage spread of 20 mw/cm². The travel medium and the manufacturing limitations result in significant energy loss, thus making the systems very inefficient.

Presently available infant warmers are power hungry and do not promote Kangaroo mother care. There is a strong desire to allow an infant warmer to be used as part of Kangaroo mother care. Such an infant warmer would need to be small in size such that the mother can hold it without disturbing the thermal neutral environment and the infant.

SUMMARY

The present disclosure is directed to an infant warming system for use with an infant patient. The infant warming system includes a light source that is operable to generate a warming light in the laser light spectrum. In one embodiment, the light source can be a laser diode (20 W, 700-1000 nm) that can be coupled to an optical fiber cable. The optical cable can transmit the warming light from the laser light source. An optical splitter can be used to divide the warming light for receipt by a plurality of optical fibers each having a fiber ending. The optical fiber cable including the fiber endings can be arranged in such a way that the laser light (in IR range) can travel from the laser light source with very little loss and can be spread evenly using an optical diffuser.

The infant warming system can include a diffuser that is positioned to receive the plurality of fiber endings and to diffuse the warming light for the fiber endings into a series of spaced warming zones. The warming zones can be positioned a predetermined distance from the infant patient to warm the infant during use of the warming system.

The diffuser can be contained within a warming blanket, which can be positioned around the infant. The infant can then be placed on the warming blanket or in a wrap. Due to the proximity of the IR rays to the infant, the infant can be warmed quickly and the energy loss will be much less.

A control circuit can be used with the infant warming system to control the operation of the light source. In an exemplary embodiment, the control circuit, power supply and light source are located remotely from the infant and the warming blanket. Further, the light source can be removably connected to the warming blanket such that one light source can be used with multiple warming blankets and moved between the warming blankets. The infant warming system can include a temperature probe positioned to detect the temperature of the infant and return the temperature to the control circuit.

In a contemplated alternate embodiment, the laser light source can be replaced with t light emitting diode that generates phototherapy light in a phototherapy light spectrum. The light therapy system can include an optical cable that can be coupled to the light emitting diode to transmit the phototherapy light from the light emitting diode. An optical splitter can be used to divide the phototherapy light for transmitting the light along a plurality of optical fibers each having a fiber ending. A diffuser can be positioned to receive the plurality of fiber endings and operable to diffuse the phototherapy light from the fiber endings into a plurality of therapy areas that can be located a predetermined distance from the infant.

As described above, the present disclosure can utilize a light source (laser diode) (20 W, 700-1000 nm) and tether an optical fiber cable to it using SMA or a diamond connector. The optical fiber cable can include a plurality of fiber endings that can be equally distributed through use of an optical diffuser to prevent any local concentration of light energy. The optical fiber diffuser can be encapsulated in a polythene flexible bag, which in turn can be inserted into a pouch of a cloth blanket or wrap that can be worn by the infant.

An infant temperature probe can be included in the wrap/blanket. The temperature probe can be the only electrical component applied to or near the infant. The temperature probe can be isolated since it will be on the secondary side of the power supply. This can be routed together with the optical fiber cable itself such that no additional cables are needed. The laser light source can be a handheld component that can be carried inside the NICU/PICU without much effort and connected to the warming blanket.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

One or more specific embodiments of the present disclosure are described below in order to provide a thorough understanding. These described embodiments are only examples of the systems and methods for providing infant warming. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide devices and methods for heating an infant patient with improved efficiency. An exemplary device includes a blanket that includes a warming element for delivering heat to an infant placed on, or at least partially surrounded by, the blanket.

In addition, a blanket integrating the heating element enables developmental care of the infant. Kangaroo care, involving skin to skin contact between the infant and the mother, is an important component of developmental care. The blanket as disclosed herein is easily portable—the infant may be carried within the blanket. The infant may be comforted and/or transported by a caregiver while the heating element is in use. The infant warming system includes a light source that is located remotely from the warming blanket and can be connected and disconnected from the warming blanket. In this manner, the light source and be disconnected from one warming blanket and connected to another warming blanket being used with another infant. This allows the warming blanket to remain with the infant before or after a warming procedure. Therefore, the developmental/Kangaroo care can be delivered without stopping the heating and without removing the warming blanket from one infant for use with another infant.

Figure 1:
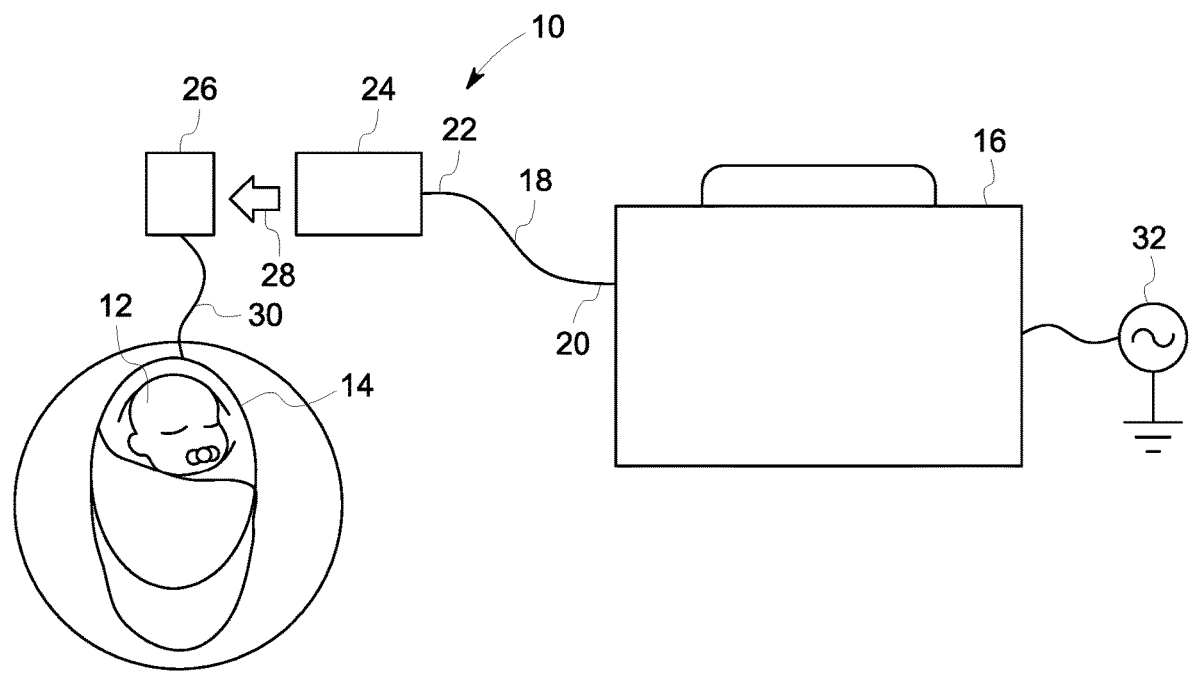
FIG. 1 is a schematic illustration of the infant warming system of the present disclosure.

FIG. 1 is a general schematic illustration of the infant warming system 10 constructed in accordance with the present disclosure. In the embodiment shown in FIG. 1, the infant warming system 10 is shown used with an infant patient 12 that is received within a warming blanket 14 that forms part of the infant warming system. The warming blanket 14 is used to swaddle the infant 12 in a manner that the infant can be held by a mother or other caregiver to promote Kangaroo care. Although use of the warming blanket 14 is desirable to promote Kangaroo care, the warming blanket 14 could be used in many other ways to provide warming to the infant. The warming blanket 14 is designed such that the mother can hold it without disturbing the thermal neutral environment created by the warming blanket 14.

The infant warming system 10 shown in FIG. 1 includes a light source 16 that is located remotely from the infant patient 12 and the warming blanket 14 and is operable to generate a source of light. The distance between the light source 16 and the warming blanket 14 can vary and depends upon the length of the connecting cable. The distance could vary from several feet to ten or more feet depending on the application for the warming system 10. In the embodiment illustrated in FIG. 1, the light source 16 creates a source of light that is transmitted away from the light source 16 through an optical output cable 18. The optical output cable 18 is connected at a first end 20 to the light source 16 while a second end 22 is connected to a first opto-electrical connector 24. The opto-electrical connector 24 provides not only a connection for the light traveling from the light source 16 but also for electrical signals and power to be transmitted across the connection between the first opto-electrical connector 24 and the second opto-electrical connector 26. The transfer of both electrical signals/power and the light from the light source 16 is shown by arrow 28 in FIG. 1.

The second opto-electrical connector 26 in turn is connected to the warming blanket 14 by an optical fiber cable 30. The optical fiber cable 30 preferably includes a plurality of optical fibers bundled together along with one or more electrical wires that allows both the optical signals and the electrical signals to be transferred from the second opto-electrical connector 26 to the warming blanket 14.

As can be understood in FIG. 1, the infant warming system 10 generally includes two primary components: namely the light source 16 and the warming blanket 14. The electrical and optical coupling that takes place between the two connectors 24, 26 allows both light and electrical signals to pass from the light source 16 to the warming blanket 14. Additionally, this connection and the lengths of both the optical output cable 18 and the optical fiber cable 30 allow the infant patient 12 to be located a distance away from the light source 16. In addition, a single light source 16 can be utilized with multiple infants by simply connecting and disconnecting each warming blanket 14 to the light source 16 through the use of the pair of connectors 24, 26. This feature allows the infant to remain in the warming blanket 14 before and after a warming procedure or event. In the embodiment shown in FIG. 1, the light source 16 is connected to a supply of power 32. However, as will be discussed in greater detail below, it is contemplated that the light source 16 could include an internal battery power supply such that the light source 16 could operate from either the power supply 32 available at the hospital or other facility or as a standalone unit utilizing the battery back up power supply.

Figure 2:
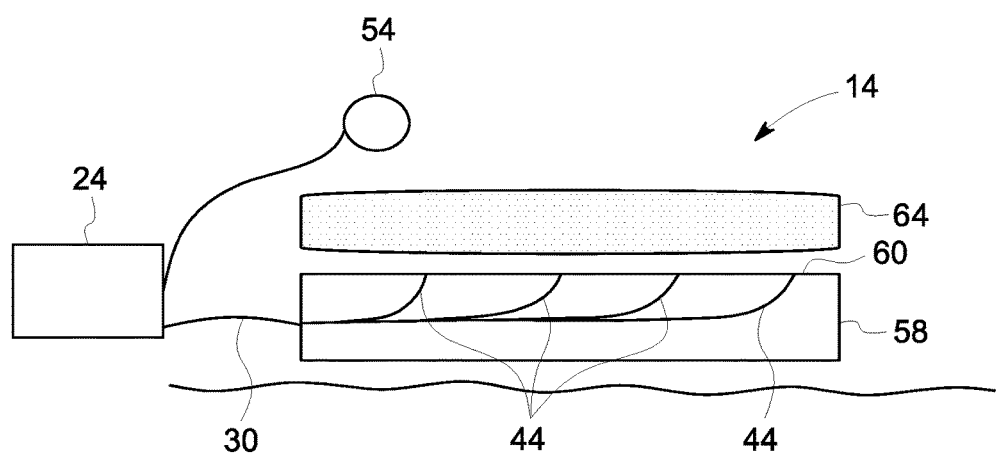
FIG. 2 is a magnified view of the infant warming blanket that operates as part of the infant warming system.

FIG. 2 is a schematic illustration of the warming blanket 14 and the connection to the connector 24. The warming blanket 14 includes a connection to the connector 24 through the optical fiber cable 30 which includes a plurality of individual optical fibers 44 that extend into a diffuser 58 to deliver heat to the infant in a manner to be described in much further detail below.

Figure 3:
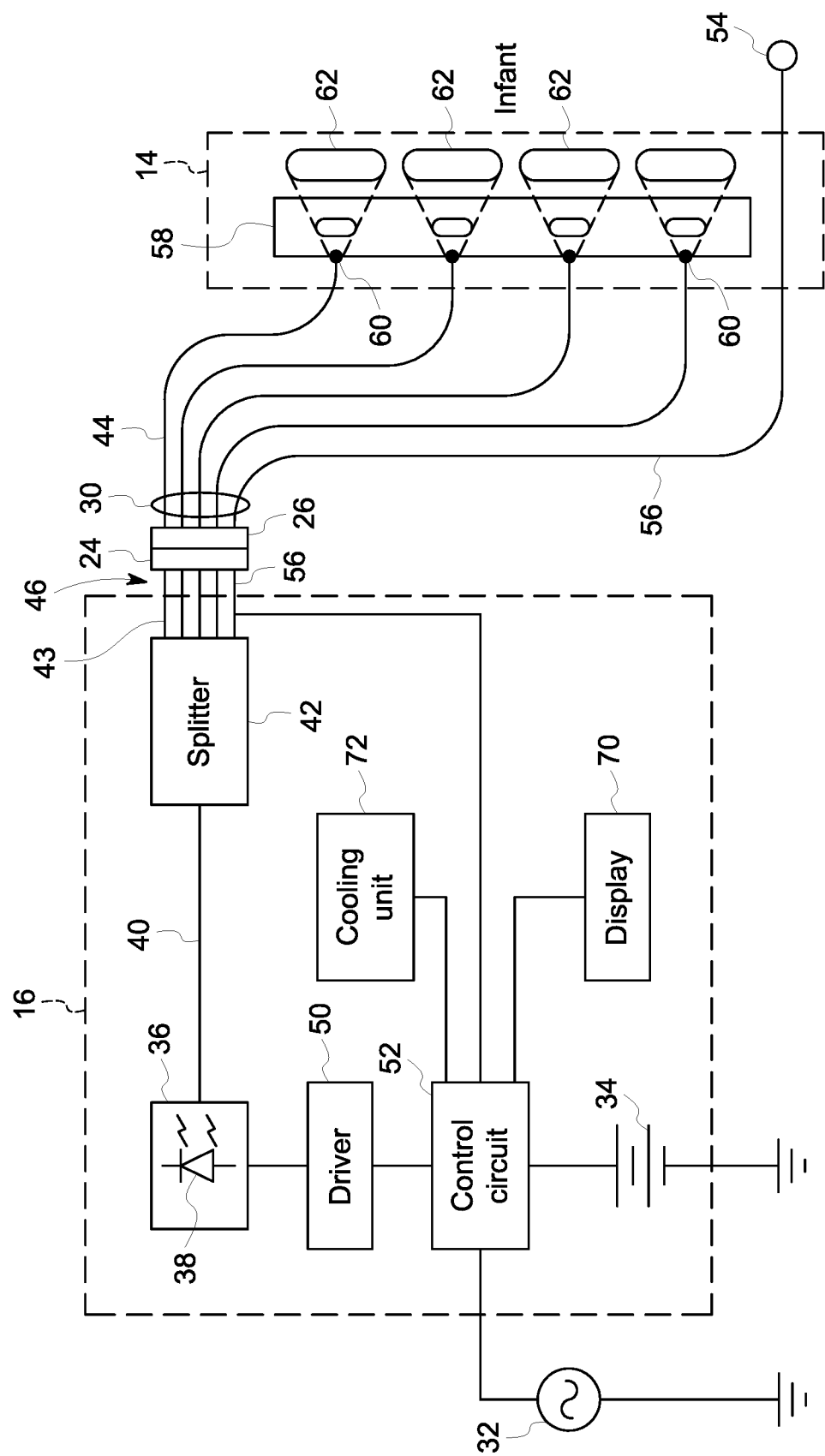
FIG. 3 is a schematic illustration of the laser light source and infant warming blanket used to provide warming to an infant.

FIG. 3 provides for additional details of the light source 16 constructed in accordance with one embodiment of the present disclosure. As illustrated in FIG. 3, the light source 16 is connected to the main power supply 32. Further, the light source 16 is shown as including a battery 34 that is self-contained within the housing that defines the light source 16.

In the embodiment of the disclosure shown in FIG. 3, the light source 16 includes a laser light source 36. The laser light source 36 includes at least one laser diode 38 that generates laser light at a selected wavelength (20 W, 700-1,000 nm as an illustrated example). The laser diode 38 generates laser light in the IR range that can travel from the laser diode over long distances with very little loss. Although a laser diode 38 is shown, other types of light sources, such as a high power IR LED are contemplated as being within the scope of the present disclosure.

The laser light source 36 is shown connected to an optical cable 40. Preferably, the connection between the laser light source 36 and the optical cable 40 is carried out using an SMA or diamond connector. The optical cable 40 provides a conduit for the laser light to travel to a splitter 42. The splitter 42 operates to split the single laser light source present in the optical cable 40 into a plurality of light sources that each travel along one of a plurality of optical fibers 44. The optical fibers 43 form part of the composite optical output cable 18. As illustrated in FIG. 3, the optical output cable 18 leaving the light source 16 includes the first opto-electrical connector 24 while the optical fiber cable 30 is connected to the second opto-electrical connector 24.

As illustrated in FIG. 3, the laser diode 38 is controlled by an LED driver 50. The LED driver provides the required power and signals to the laser diode 38 in a well-known manner. The LED driver 50, in turn, is operatively connected to a control circuit 52. The control circuit 52 is thus able to control the LED driver 50 and the laser diode 38.

In addition to the control of the LED driver 50 and the laser diode 38, the control circuit 52 is also connected to a temperature probe 54 through a control cable 56 that passes through the pair of connectors 18, 24. The temperature probe 54 can be placed in close contact with the infant and operates to provide a temperature signal back to the control circuit 52 such that the control circuit 52 can control the operation of the LED driver 50 and thus the laser diode 38. In addition to controlling the operation of the LED driver 50 and the laser diode 38, the control circuit 52 can be operated to regulate the temperature of the infant and can perform alarm management functions to alert the clinician of errors or alarm conditions that may occur regarding the operation of the warming blanket 14.

In the embodiment shown in FIG. 3, the control circuit 52 is connected to both the main power supply 32 and the battery 34. The battery 34 can be used in applications in which a main power supply 32 is unavailable or when the main power supply 32 is interrupted. The battery 34 can include a charging circuit (not shown) such that whenever the light source 16 is connected to the main power supply 32, the battery 34 is continuously charged.

Figure 4:
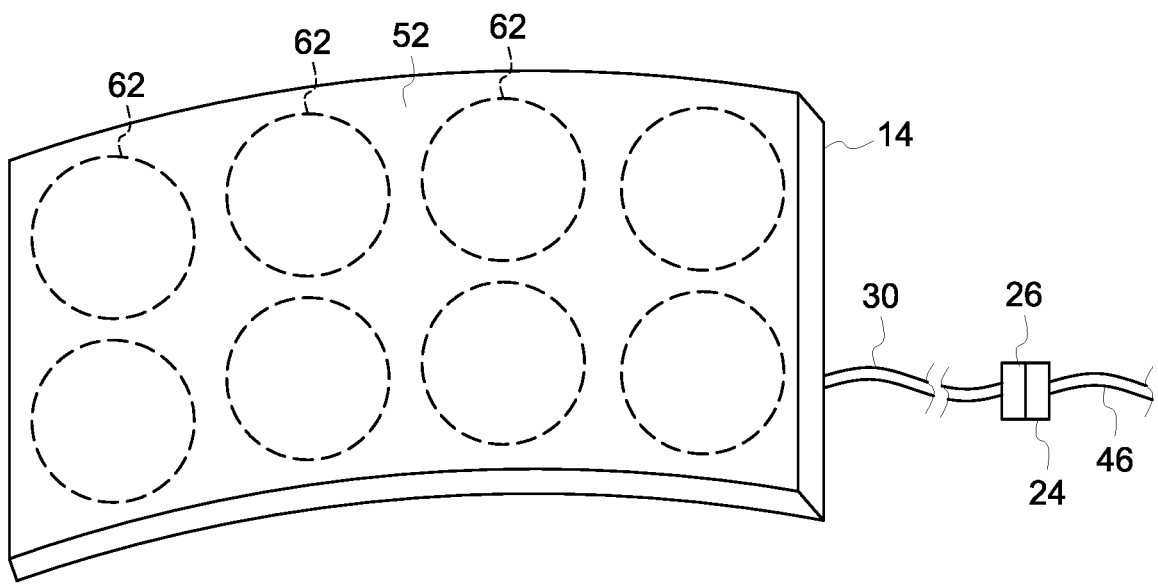
FIG. 4 is a top view of a warming blanket illustrating the warming zones.

FIG. 4 includes a more detailed view of the warming blanket 14 that forms part of the infant warming system. As illustrated in FIGS. 3 and 4, the optical cable 30 coming from the second opto-electrical connector 24 includes a plurality of optical fibers 44 that each enter into a diffuser 58. The individual optical fibers 44 are distributed along the length and width of the diffuser 58. Each of the optical fibers 44 includes a fiber ending 60. The fiber ending 60 allows light traveling along the individual fiber 48 to leave the fiber. As illustrated in FIG. 3, the diffuser 58 is designed to receive the laser light from the fiber ending 60 and to diffuse the laser light into a broader warming zone 62. In the embodiment shown in FIG. 4, the diffuser 58 includes eight separate warming zones 62 spaced along the length and width of the warming blanket 14. Although eight warming zones 62 are shown in FIG. 4, the diffuser can include any suitable number of separate warming zones 62, such as four zones, six zones or ten zones, among other possible configurations. The number and location of the warming zones 62 can vary based upon the size of the warming blanket and user requirements. The diffuser 58 is designed such that the warming zones 62 essentially cover the entire length and width of the diffuser 58 to create a uniform heating area for contact with the infant. The fiber endings 60 are positioned close enough together to create a "blanket" of warmth that is supplied to the infant patient. The warming light from each of the optical fibers 44 passes through the diffuser 58 to create the warming zone 62, which are designed to touch each other to create complete coverage of the infant patient. In some examples, any suitable subset of the number of warming zones 62 can provide this breadth of heating coverage.

Figure 5:
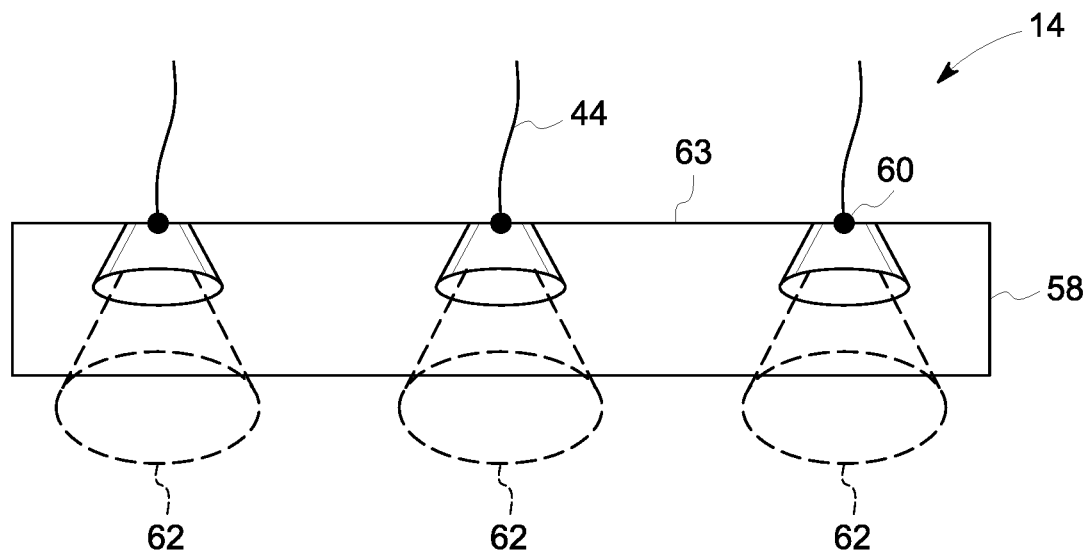
FIG. 5 is a magnified view of the diffuser.

FIG. 5 illustrates a magnified view of the diffuser 58. As illustrated in FIG. 5, the fiber ending 60 contacts a diffuser surface 63 that acts to diffuse the light outward to create the heating zone 62. Three of the individual heating zones 62 are shown in FIG. 5. However, it should be understood that a different number of optical fibers 44 and diffuser areas/ heating zones 62 could be incorporated into the diffuser 58. In the embodiment illustrated, the optical fibers 44 can be formed from a high-temperature plastic material that can include a protective sheath that will help to prevent breakage of the optical fiber 44. In one contemplated embodiment, the core diameter of the optical fiber can be 400 um and the NA 0.22 The combination of the heating zones 62 created by the warming light from the optical fibers is designed to generate approximately 30 mW/cm$^2$.

Figure 6:
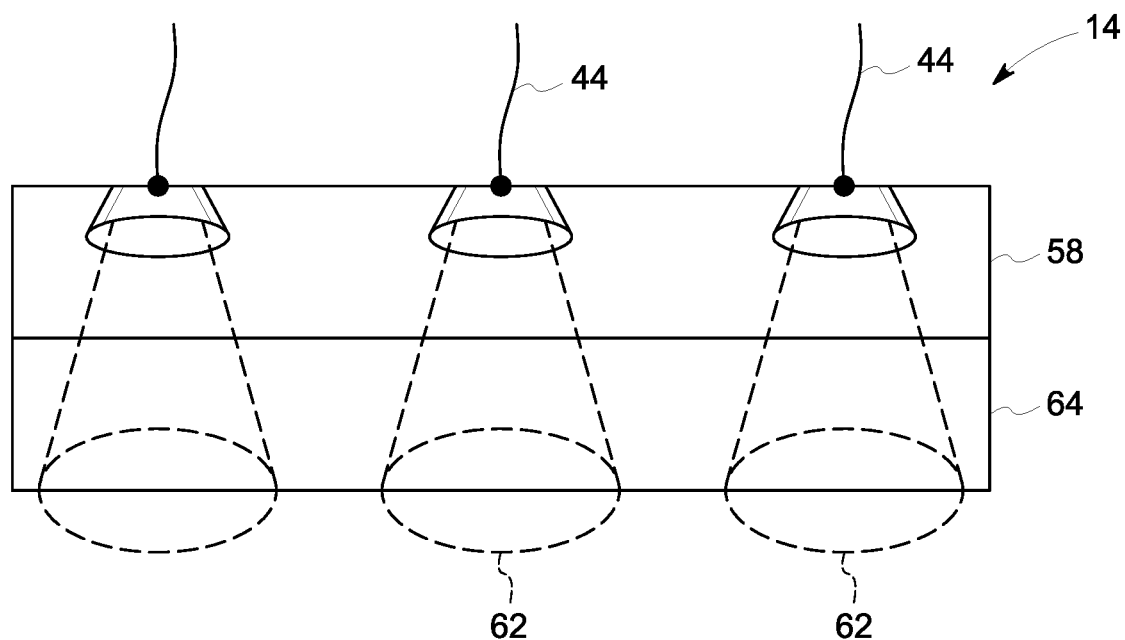
FIG. 6 is a magnified view of the diffuser when used with a spacer.

FIG. 6 illustrates an alternate embodiment in which the diffuser 58 is positioned above a spacer 64. The spacer 64 is designed of a material that acts to further diffuse the light from each of the individual optical fibers 44 to expand the size of the warming zones 62. Although the spacer 64 is shown in FIGS. 2 and 6, it should be understood that the warming blanket 14 could be constructed with or without the spacer.

Referring back to FIG. 3, the light source 16 can further include a display 70. The display 70 can be used to provide a basic interface in which the operator can both view and set the desired baby temperature as well as control the output power from the laser diode 38. It is contemplated that there will be at least two primary modes of operation that can be controlled through commands and information enter into the display 70. In a first mode, the clinician can set a desired intensity of heating that is supplied to the infant patient. In a second, servo mode, the clinician can select a desired patient temperature and the control circuit can control operation to control the monitored temperature of the infant patient. As also shown in FIG. 3, the light source 16 can include a cooling unit 72 that is operable to cool the laser diode 38 to a temperature below room temperature. The cooling unit 72 could be a Peltier module that is controlled in an on/off state by the control unit 52. Various different types of cooling units 72 could be utilized to maintain the temperature of the light source 16 at a desired operating temperature while operating within the scope of the present disclosure.

As can be understood by the described drawing figures, the light source 16 can be separated from the warming blanket 14 such that a single light source could be utilized with multiple different warming blankets 14. In this manner, the warming blanket 14 could stay wrapped around the infant patient and the light source 16 can be moved between patients in an intensive care unit or other ward within a hospital. As can be further understood in FIG. 3, the only electrical device placed in contact with the infant is the temperature probe 54, which is a low voltage device. The optical fibers 44 provide the source of laser light to the diffuser 58 and eliminates any type of galvanic connection located near the infant patient. In addition, since the warming blanket 14 is wrapped around the infant, the warming blanket 14 reduces any risk of unintended water loss since the infant is wrapped and convection heat loss is reduced considerably.

In the embodiment illustrated in the drawing figures, the light source 36 includes a laser diode. However, it is contemplated that the laser diode 38 could be replaced with a diode that generates blue light for phototherapy. Phototherapy is an effective method for treating neonatal hyperbilirubinemia where bilirubin molecules absorb light in the blue spectra (e.g., wavelength of 425-475 nm) and convert into water soluble isomers which are then excreted by the body. For phototherapy treatment to be effective, the blue light needs to penetrate the skin to reach bilirubin molecules in the blood.

As an example, the laser diode 38 could be replaced with a blue light source that delivers light in the blue spectra (e.g., wavelength of 425-475 nm, among others). In such an embodiment, the light emitted by the phototherapy diode may be diffused and supplied to the infant patient in a similar manner as described at each of the diffusion areas/warming zones 62. However, since the laser diode would be replaced with a photodiode of a blue light wavelength, the areas 62 would provide phototherapy to the infant patient rather than warming.

In such an embodiment, the control circuit 52 may include a pulse width modulation (PWM) controller that is operable to control the blue light source. During phototherapy treatment of a patient, the intensity of light delivered to the patient can be controlled by the duty cycle of the operation of the light source 36, which is controlled by the PWM controller. Other control techniques to control the intensity of the light delivered are contemplated as being within the scope of the present disclosure. In the described embodiment, in order to increase the intensity of therapy light delivered to the patient, the duty cycle of the light source 36 is increased through use of the PWM controller.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. An infant warming system for use with an infant, comprising:
a light source operable to generate a warming light in a laser light spectrum;
an optical cable coupled to the light source to transmit the warming light from the light source;
an optical splitter operable to divide the warming light for receipt by a plurality of optical fibers each having a fiber ending; and
a flexible diffuser designed to be contained within a warming blanket that can be placed in direct contact with the infant, wherein the flexible diffuser receives the plurality of fiber endings at a plurality of spaced locations along the flexible diffuser and diffuses the warming light directly from the fiber endings to create a series of warming zones spaced along an outer surface of the flexible diffuser.

2. The infant warming system of claim 1 further comprising a control circuit operatively coupled to the light source to control operation of the light source.

3. The infant warming system of claim 2 wherein the control circuit is connected to a power supply and wherein the control circuit, power supply and light source are located remote from the infant.

4. The infant warming system of claim 3 further comprising a temperature probe positionable on or near the infant to detect the temperature of the infant, wherein the temperature probe is connected to the control circuit.

5. The infant warming system of claim 1 wherein the plurality of optical fibers are contained in an optical fiber cable coupled at a first end to the diffuser and having a first opto-electrical connector on a second end.

6. The infant warming system of claim 5 wherein the optical fiber cable coupled to the light source includes a second opto-electrical connector such that the warming blanket and the light source are connectable with the first and second opto-electrical connectors.

7. An infant warming system for use with an infant, comprising:
a laser light source located remotely from the infant patient and operable to generate a warming light in a laser light spectrum;
a plurality of optical fibers that each receive the warming light and transmit the warming light to a fiber endings on each of the plurality of optical fibers; and
a warming blanket positionable in contact with the infant to provide heat to the infant, the warming blanket including a flexible optical diffuser that receives the plurality of fiber endings at spaced locations along the flexible optical diffuser to directly diffuse the warming light to create a plurality of warming zones spaced along an outer surface of the flexible optical diffuser to create a source of heat for the infant patient.

8. The infant warming system of claim 7 wherein the laser light source is a laser diode.

9. The infant warming system of claim 8 wherein the laser light source includes a control circuit and a power supply, wherein the control circuit controls the application of the power supply to the laser diode.

10. The infant warming system of claim 8 wherein the laser light source includes an optical splitter to divide the warming light and connect the warming light to the plurality of optical fibers.

11. The infant warming system of claim 7 wherein the plurality of optical fibers are contained in an optical fiber cable coupled at a first end to the diffuser and having a first opto-electrical connector on a second end.

12. The infant warming system of claim 11 wherein the optical cable coupled to the light source includes a second opto-electrical connector such that the warming blanket and the light source are connectable with the first and second opto-electrical connectors.

13. The infant warming system of claim 7 further comprising a cooling unit operable to cool the temperature of the laser light source.

\* \* \* \* \*